(12) United States Patent
Nagae et al.

(10) Patent No.: US 12,302,935 B2
(45) Date of Patent: May 20, 2025

(54) THREE-LAYERED CAPSULE CONSTRUCTED WITH NON-HYDROGENATED OIL AND PRODUCTION THEREOF

(71) Applicant: MORISHITA JINTAN CO., LTD., Osaka (JP)

(72) Inventors: Kentaro Nagae, Hirakata (JP); Hisaaki Hatanaka, Hirakata (JP)

(73) Assignee: MORISHITA JINTAN CO., LTD., Osaka (JP)

( * ) Notice: Subject to any disclaimer, the term of this patent is extended or adjusted under 35 U.S.C. 154(b) by 552 days.

(21) Appl. No.: 16/652,633

(22) PCT Filed: Nov. 21, 2018

(86) PCT No.: PCT/JP2018/042993
§ 371 (c)(1),
(2) Date: Mar. 31, 2020

(87) PCT Pub. No.: WO2019/111711
PCT Pub. Date: Jun. 13, 2019

(65) Prior Publication Data
US 2020/0236984 A1   Jul. 30, 2020

(30) Foreign Application Priority Data

Dec. 8, 2017 (WO) ................. PCT/JP2017/044121

(51) Int. Cl.
| A23P 10/35 | (2016.01) |
| A23L 29/231 | (2016.01) |
| A23L 29/281 | (2016.01) |
| A23L 33/135 | (2016.01) |

(52) U.S. Cl.
CPC ............ *A23P 10/35* (2016.08); *A23L 29/231* (2016.08); *A23L 29/284* (2016.08); *A23L 33/135* (2016.08); *A23V 2002/00* (2013.01)

(58) Field of Classification Search
CPC ...... A23P 10/35; A23L 29/231; A23L 29/284; A23L 33/135; A23L 29/256; A23L 29/269; A23L 33/15; A23L 5/00; A23L 33/10; A23V 2002/00; A23V 2200/224; A23V 2200/3204; A23V 2250/194; A61K 9/4816; A61K 9/4808; A61K 9/5073; B01J 13/04; A23Y 2300/00
USPC ......................................................... 426/61
See application file for complete search history.

(56) References Cited

U.S. PATENT DOCUMENTS

| 5,330,835 A | 7/1994 | Kikuchi et al. |
| 2004/0175412 A1 | 9/2004 | Asada et al. |
| 2011/0002902 A1* | 1/2011 | Asada ............... A61P 13/12 435/252.9 |
| 2013/0089531 A1 | 4/2013 | Asada et al. |

FOREIGN PATENT DOCUMENTS

| JP | H05-031352 | | 2/1993 |
| JP | 2001238611 A | * | 9/2001 |
| JP | 2006-129715 | | 5/2006 |
| JP | 2006-316254 | | 11/2006 |
| JP | 5184722 B1 | | 4/2013 |
| JP | 5487379 | | 5/2014 |
| JP | 2015-145341 | | 8/2015 |
| JP | 2016-074615 | | 5/2016 |
| JP | 2016074615 A | * | 5/2016 |
| JP | 2016-208969 | | 12/2016 |
| KR | 10-2004-0014584 | | 2/2004 |
| WO | WO2013/061671 | | 5/2013 |
| WO | 2017/005887 A1 | | 1/2017 |

OTHER PUBLICATIONS

NPL Olein (in Science Direct: From: Hydrogenation of Fats and Oils (second Edition) 2011) (Year: 2011).*
NPL Palm oil (Retrieved on Nov. 18, 2022). (Year: 2022).*
Google search report retrieved on Nov. 18, 2022. (Year: 2022).*
NPL Palm hydrogenated vs non-hydrogenated (Retrieved on Sep. 14, 2023). (Year: 2023).*
Kohno, Mamiko et al., "Application of enteric seamless capsules containing Bifidobacterium longum to functional foods," Folia Pharmacologica Japonica, vol. 148, 2016, p. 310 314, relevant information provided in the attached International Search Report of PCT/JP2017/044121.
International Search Report of PCT/JP2018/042993, Feb. 26, 2019, 3 pages including English translation.
International Search Report of priority application, PCT/JP2017/044121, Mar. 13, 2018, 4 pages including English translation.
Sandeep Kalepu et al., "Oral lipid-based drug delivery systems—an overview," Acta Pharmaceutica Sinica B, vol. 3, Issue 6, Elsevier B.V., 2013, pp. 361-372.
Office Action issued for Taiwanese Patent Application No. 107143447, 8 pages with English translation.
Bailey's Industrial Oil And Fat Products, edited by Shahidi (Canada); translated by Wang Xingguo and Jin Qingzhe, pp. 227-228, Beijing; China Light Industry Press, 6th Edition; with English translation.
Office Action issued for Chinese Patent Application No. 201880063102. 4, Jan. 19, 2023, 22 pages with English translation.

(Continued)

*Primary Examiner* — Erik Kashnikow
*Assistant Examiner* — Bhaskar Mukhopadhyay
(74) *Attorney, Agent, or Firm* — HSML, P.C.

(57) ABSTRACT

The present invention is to inhibit the cracks of the protective layer when producing the three-layered capsules and to solve the problems of cracks when producing and storing in the cooled condition to provide a three-layered capsule and a production thereof without suck generation of cracks.
The present invention provides a three-layered capsule which comprises:
  a content comprising a main agent dispersed or solubilized in oil material,
  a protective layer, formed on the content, comprising edible refined and processed oil, and
  a shell, formed on an outside the protective layer, comprising natural polymer, the three layers being present concentrically, and a producing method of the capsule.

11 Claims, 4 Drawing Sheets

(56) References Cited

OTHER PUBLICATIONS

Office Action issued for Korean Patent Application No. 10-2020-7007116, Mar. 21, 2024, 18 pages including machine translation.
Nils Hinrichsen, "Commercially available alternatives to palm oil", Lipid Technology, vol. 28, No. 3-4, Apr. 14, 2016, pp. 65-67; available at: https://doi.org/10.1002/lite.201600018.
Office Action issued for Canadian Patent Application No. 3075986, dated Jan. 30, 2024, 7 pages.
Office Action issued in Canadian Patent Application No. 3,075,986, Mar. 4, 2025 (6 pages).

\* cited by examiner

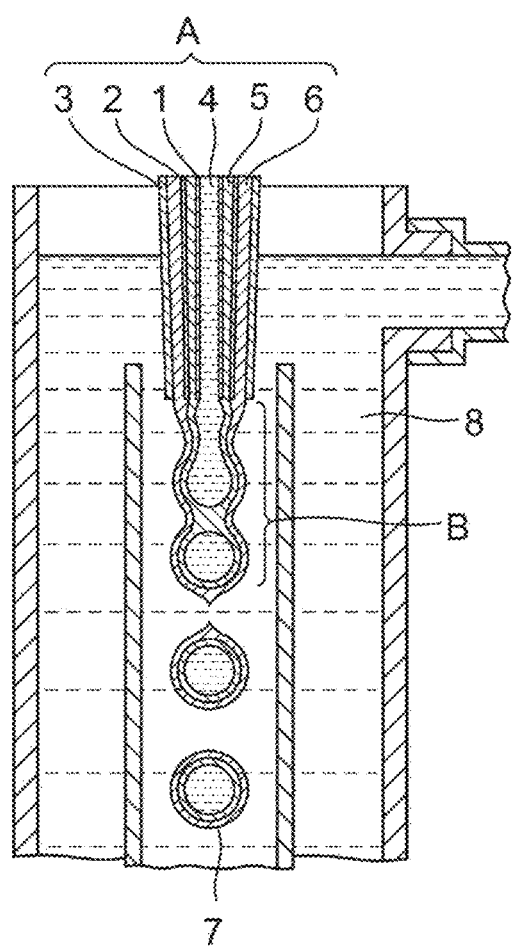
[Fig. 1]

THREE-LAYERED CAPSULE CONSTRUCTED WITH NON-HYDROGENATED OIL AND PRODUCTION THEREOF

TECHNICAL FIELD

The present invention is related to a three-layered capsule and a production thereof, more particularly to a three-layered capsule reducing cracks which occur at a time of production or at a time of storing it at lower temperatures and a production thereof.

BACKGROUND ART

Seamless capsules are employed for many applications, in view of easy control of capsule size, easy production of the capsules, and the like. Commercially available are capsules encapsulating useful bacteria, such as *Bifidobacterium* and the like or capsules containing flavor, such as menthol and the like. These capsules are generally produced by a process ejecting liquid droplets from double nozzles or triple nozzles of a solution of a content or a solution of a shell into a cooling solution (generally, oily substance) which is flowing.

For example, JP H0769867 A (Patent Literature 1) and JP 2016074615 A (Patent Literature 2) disclose a production of three-layered seamless capsules wherein a solution of a content in which a main agent and a hardened oil (a hydrogenated oil) are contained is ejected from an innermost nozzle of the triple nozzle, a solution of a protective layer formed from another hardened oil is ejected from an intermediate nozzle and a shell solution is ejected from an outermost nozzle, simultaneously into a cooling solution.

When producing the seamless capsules, there is a problem of generation of cracks in the protective layer because of rapid cooling, since the capsule jet ejected from the triple nozzle is ejected into the cooling solution of not more than 10° C. and thus rapidly cooled in the cooling solution to solidify. Generation of cracks is also observed when the capsules are stored at cooling conditions (e.g. a temperature of −20° C. to 5° C.).

CITATION LIST

Patent Literature

[PTL 1]
  JP H05-31352 A
[PTL 2]
  JP 2016-74615 A

SUMMARY OF INVENTION

Technical Problem

The present invention is to inhibit the cracks of the protective layer when producing the three-layered capsule and to solve the problems of cracks when producing and storing in the cooled condition to provide the three-layered capsule and a production thereof without cracks.

Solution to Problem

The inventors of the present invention study intensively for solving the above problem and have found that edible refined and processed oil is employed in the solution of the content and/or the protective layer of the three-layered capsule to effectively prevent the cracks to achieve the present invention.

Thus, the present invention is to provide three-layered capsule which comprises:
  a content comprising a main agent dispersed or solubilized in oil material,
  a protective layer, formed on the content, comprising edible refined and processed oil, and
  a shell, formed on an outside of the protective layer, comprising natural polymer, the three-layers being present concentrically, wherein
  the oil material is selected from the group consisting of edible plant oil, edible refined and processed oil, sucrose fatty acid ester, glycerol fatty acid ester and a mixture thereof,
  the edible refined and processed oil is non-hydrogenated oil having a melting point of 15 to 55° C. and a solid fat content (SFC) of 30 to 90% at 10° C., 0.3 to 80% at 20° C., 0.1 to 70% at 30° C., 0.3 to 40% at 40° C., 0.3 to 30% at 45° C., and
  the non-hydrogenated oil is selected from the group consisting of palm stearin, palm olein, palm super olein, palm double olein, palm mid fraction, which are fractionating from palm oil; an ester-exchanged oil of palm oil or the fractionated palm oil; and a mixture thereof.

The present invention also provides a process for producing the three-layered capsule, comprising ejecting into cooling solution formed from cooled liquid oil, a solution of a content from an innermost nozzle of a concentric triple nozzles, the content comprising a main agent dispersed or solubilized in oil material, ejecting a protective layer solution comprising edible refined and processed oil from an intermediate layer outside of the innermost nozzle, and ejecting a solution of natural polymer comprising natural polymer from an outermost nozzle, in a droplet form, to form a three-layered capsule, wherein
  the oil material is selected from the group consisting of edible plant oil, edible refined and processed oil, sucrose fatty acid ester, glycerol fatty acid ester and a mixture thereof,
  the edible refined and processed oil is non-hydrogenated oil having a melting point of 15 to 55° C. and a solid fat content (SFC) of 30 to 90% at 10° C., 0.3 to 80% at 20° C., 0.1 to 70% at 30° C., 0.3 to 40% at 40° C., 0.3 to 30% at 45° C., and
  the non-hydrogenated oil is selected from the group consisting of palm stearin, palm olein, palm super olein, palm double olein, palm mid fraction, which are fractionating from palm oil; an ester-exchanged oil of palm oil or the fractionated palm oil; and a mixture thereof.

In order to conduct the present invention, the following embodiments are also considered:
  The natural polymer is water soluble.
  The natural polymer is selected from the group consisting of gelatin, agar, gellan gum, carrageenan, furcellaran, pectin, chitosan, alginic acid, curdlan, starch, modified starch, pullulan, mannan and a mixture thereof.
  The three-layered capsule is a seamless capsule.
  The protective layer has a melting point being 2 to 9° C. higher than that of the content.
  The main agent is selected from the group consisting of *Bifidobacterium, Lactobacillus*, lactoferrin, nattokinase, vitamin C, vitamin B1, vitamin B2, vitamin B12 and a mixture thereof.

Advantageous Effects of Invention

According to the present invention, cracks occurring at the time of production of the three-layered capsules are effectively prevented by employing the edible refined and processed oil, especially non-hydrogenated oil in the protective layer of the three-layered capsule. The cracks are also generated when the capsules are stored at a cooling condition (e.g. storing at a temperature of not more than 10° C.) to reduce protective effects of the content of the capsule and thus to lead to poor storage stability, but the three-layered capsules of the present invention do not arise cracks when they are stored at a cool condition.

Hitherto, when producing the three-layered capsules, hardened oil has been generally employed as the protective layer for protecting the capsule content. The hardened oil (hardened fat and oil) is meant a fat and oil in solid form at ambient temperature obtained by modifying a fat and oil in solution at ambient temperature, containing unsaturated fatty acid having relatively low melting point in a rather large amount, by adding hydrogen (hydrogenating), to increase an amount of saturated fatty acid having higher melting point. The hardened oil includes, e.g. complete hydrogenated oil (or fat and oil) and partially hydrogenated oil (or fat and oil). On the other hand, in a paper named "European Journal of Clinical Nutrition (2009) 63, S22 to S33", it is reported that partially hydrogenated fat and oil shows possibility of heart disease. Food and Drug Administration (FDA) in USA indicates an amount of administrating trans fatty acid in one day and a limited amount of partially hydrogenated oil (or fat and oil) employed in food. In response to the FDA activity, consumers in USA try to refuse use of partially hydrogenated oil (or fat and oil) and their number are increased. And many consumers have recently refused products merely presenting a phrase of "hydrogenated". According to the present invention, non-hydrogenated oil (fat and oil) is employed and the three-layered capsules of the present invention can be accepted by such consumers who refuse the use of "hydrogenated" oil.

BRIEF DESCRIPTION OF DRAWINGS

FIG. 1 is a schematic cross section of a nozzle portion of a production apparatus for producing the three-layered seamless capsule by a droplet dropping method using a triple nozzle.

FIG. 2-1 represents an enlarged photograph of a seamless capsule having cracking which is obtained in Comparative Example 1 and FIG. 2-2 is a schematic drawing easily viewing the cracking, as the photograph of FIG. 2-1 is a little difficult to see.

FIG. 3-1 represents in another angle an enlarged photograph of a seamless capsule having cracking which is obtained in Comparative Example 1 and FIG. 3-2 is a schematic drawing easily viewing the cracking, as the photograph of FIG. 3-1 is a little difficult to see.

FIG. 4-1 represents an enlarged photograph of a seamless capsule without cracking which is obtained in Example 1 and FIG. 4-2 is a schematic drawing similar to FIGS. 2-2 and 3-2.

DESCRIPTION OF EMBODIMENTS

Figures 1, 2:
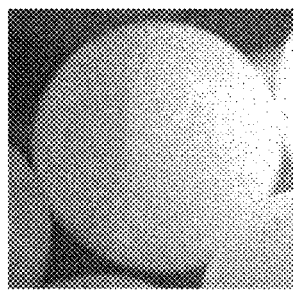
Figure 2:
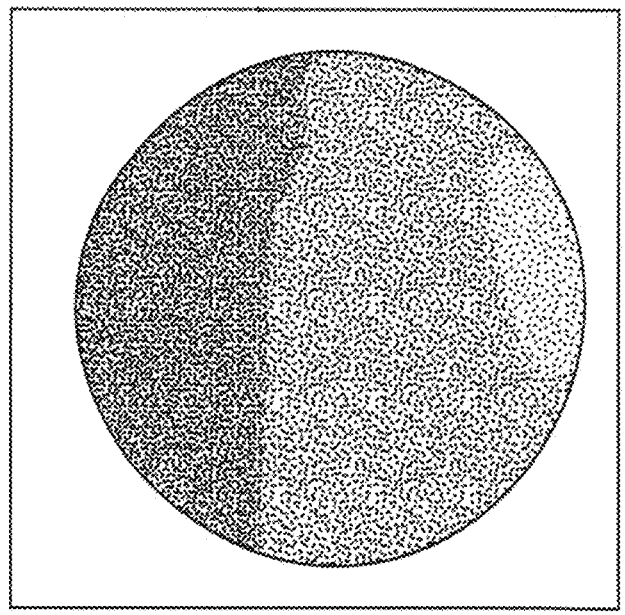

The three-layered capsule of the present invention comprises:
a content comprising a main agent dispersed or solubilized in oil material,
a protective layer, formed on the content, comprising edible refined and processed oil, and
a shell, formed outside the protective layer, comprising natural polymer, which are present concentrically, wherein
the oil material is selected from the group consisting of edible plant oil, edible refined and processed oil, sucrose fatty acid ester, glycerol fatty acid ester and a mixture thereof,
the edible refined and processed oil is non-hydrogenated oil having a melting point of 15 to 55° C. and a solid fat content (SFC) of 30 to 90% at 10° C., 0.3 to 80% at 20° C., 0.1 to 70% at 30° C., 0.3 to 40% at 40° C., 0.3 to 30% at 45° C., and
the non-hydrogenated oil is selected from the group consisting of palm stearin, palm olein, palm super olein, palm double olein, palm mid fraction, separated from palm oil, an ester-exchanged fatty acid of palm oil, an ester-exchanged oil of palm separated oil and a mixture thereof.

The main agent encapsulated in the three-layered capsule of the present invention can be anyone which is generally encapsulated in a capsule and is not limited, but includes useful bacteria in intestine, proteins, enzymes, vitamins and the like. Concrete examples thereof are selected from the group consisting of *Bifidobacterium*, *Lactobacillus*, lactoferrin, nattokinase, vitamin C, vitamin B1, vitamin B2, vitamin B12 and a mixture thereof.

The main agent is needed to disperse in an oil material. The reason why the main agent is dispersed in the oil material is that the content of the capsule is not affected in presence of a lot amount of water when producing the capsule. In the present invention, the oil material can be selected from the group consisting of edible plant oil, edible refined and processed oil, sucrose fatty acid ester (SAIB), glycerol fatty acid ester and a mixture thereof.

The edible refined and processed oil, which can also be used for the protective layer mentioned hereinafter, is a fat and oil (which is sometimes called "oil" simply), according to Japanese Agricultural Standards of edible refined and processed oil (Dec. 24, 2013, Ministry of Agriculture, Forestry and Fisheries, Notification No. 3115), of which melting point is adjusted to a melting point suitable for food application, by technique, such as applying to animal fat and oil, plant fat and oil and a mixture thereof by "hydrogenating (adding hydrogen to saturate unsaturated fatty acid for adjusting its melting point)", "fractionating (conducting fractionating operation by centrifuging, filtering or adding dropwise to portions having different melting points, hardness and content of solid fat and oil)" or "ester-exchanging (changing composition of fatty acid by using catalyst to control melting point)." The edible refined and processed oil employed for the content of the present invention can especially be a fat and oil which is not hydrogenated (specifically called as "non-hydrogenated oil (or fat and oil). The non-hydrogenated fat and oil is, as mentioned above, a fat and oil which is not modified by adding hydrogen to natural fat and oil to control melting point, including fat and oil which has been fractionated or ester-exchanged. The term "melting point" in the present specification means a rising melting point (a temperature which starts rising in a capillary by softening when fat and oil is heated).

The non-hydrogenated oil employed in the present invention is a fat and oil which has not been chemically added with hydrogen (so-called not been hydrogenated), preferably palm oil type fat and oil. The palm oil mainly contains palmitic acid and oleic acid and the two fatty acids are occupied in an amount of not less than 80% in compositional ratio, semi-solid at a room temperature. The palm oil is separated (or fractionated) with a specific temperature to obtain a liquid oil having low melting point and a solid oil having high melting point. The liquid oil with low melting point mainly contains oleic acid and the solid oil with high melting point mainly contains palmitic acid. The liquid oil is conventionally called as palm olein and the solid oil is conventionally called as palm stearin (not being called as palm palmitin although palmitic oil is contained in a large amount in its composition). In addition, palm oil can also be ester-exchanged to obtain non-hydrogenated fat and oil having a desired melting point. The non-hydrogenated oil employed in the present invention can include a fractionated oil of palm oil and an ester-exchanged oil of palm oil or the fractionated palm oil which can be used independently or mixed.

The non-hydrogenated oil employed in the present invention has a melting point of 15 to 55° C. and a solid fat content (SFC) of 30 to 90% at 10° C., 0.3 to 80% at 20° C., 0.1 to 70% at 30° C., 0.3 to 40% at 40° C., and 0.3 to 30% at 45° C. The SFC (solid fat content) can be determined according to the NMR method (provisional 3-1983 provisional solid fat content) described in the standard fat and oil analysis test method (II) established by the Japan Oil Chemists' Society. Since the non-hydrogenated oil generally has a solid fat content (SFC) of not more than 90% at a temperature of not more than 10° C., cracking of the capsule does not occur in the protective layer in the case where they are rapidly cooled at not more than 10° C., thus the capsules keeping in high quality. In addition, since the non-hydrogenated oil is not an oil modified by hydrogen, it does not provide anxiety to persons who are very sensitive to the term "hydrogenated".

The non-hydrogenated oil employed in the present invention includes palm stearin, palm olein, palm super olein, palm double olein, palm mid fraction, which are obtained by separating (or fractionating) from palm oil; an ester-exchanged fatty acid of palm oil, an ester-exchanged of fractionated palm oil; and a mixture thereof. It is not always limited thereto.

The oil material employed in the present invention can be sucrose fatty acid ester (e.g. SAM, sucrose acetate isobutyrate) or glycerol fatty acid ester. The sucrose fatty acid ester is sucrose of which hydroxyl groups are reacted with fatty acid (such as stearic acid or oleic acid) and the like, which has generally been employed as an emulsifier. The glycerol fatty acid ester is what one or two hydroxyl group(s) of glycerol are esterified with fatty acid, which has also been employed as an emulsifier. What all of the three hydroxyl groups of glycerol are reacted with fatty acid is generally called as fat or fat and oil, which is different from the glycerol fatty acid ester. The oil material employed in the present invention can be edible plant oil, edible refined and processed oil, sucrose fatty acid ester, glycerol fatty acid ester and a mixture thereof.

In the three-layered capsule of the present invention, the main agent can be contained in an amount of 1 to 50% by mass, preferably 5 to 30% by mass, more preferably 10 to 20% by mass in the content. Amounts of more than 50% by mass leads to difficulty of encapsulation and those of less than 1% by mass do not provide technical effects of the main agent. The content of the three-layered capsule of the present invention may contain a diluting agent, a stabilizer, a surfactant, an adjuvant, a foaming agent or the like. The amounts of such additive do not have any limitation, but do not inhibit the activity of the three-layered capsule of the present invention.

In the three-layered capsule of the present invention, the protective layer is formed on the outside of the content. The protective layer can also be the edible refined and processed oil which is employed in the content, especially the non-hydrogenated oil. In order to control curing (solidifying) when cooling, the protective layer has a melting point being 2 to 9° C., preferably 2 to 8° C., higher than that of the content. If the melting point is less than 2° C., mixing the content with the protective layer would easily happen when cooling and if it is more than 9° C., the protective layer does not solidify when cooling and do not easily form the capsules.

The protective layer and the content may include lecithin or silicon dioxide, to control surface tension, viscosity or specific weight. The content of the additive may not be limited, but do not inhibit the activity of the three-layered capsule of the present invention.

The protective layer is further covered with the shell. The shell contains natural polymer. The natural polymer is generally water soluble and is, for example, selected from the group consisting of gelatin, casein, zein, pectin or derivative thereof, alginic acid or salt thereof, agar, gellan gum, carrageenan, furcellaran, chitosan, curdlan, starch, modified starch, pullulan, mannan and a mixture thereof, but it is not limited thereto. These natural polymers may be contained in an amount of 50 to 90% by weight based on the solid content weight of the shell composition of the three-layered capsule.

The capsule shell may contain a plasticizer to impart flexibility in dried conditions. Examples of the plasticizer are glycerol, sorbitol and the like. The plasticizer may be present in the capsule shell in an amount of 1 to 50% by mass, preferably 5 to 40% by mass, more preferably 15 to 30% by mass, based on a total weight of dried shell. When an amount is less than 1% by mass, the capsule shell is not resistant against vacuum drying and does not show enough flexibility after the shell is dried, to result in cracking of shell. When it is more than 50% by mass, the capsule shell is too soft and would be adhered with each other or would melt at an elevated temperature.

The shell of the three-layered capsule of the present invention may further contain any additive, such as a flavor, a sweetener, a colorant, or a preservative (such as paraben). When the additive is employed, a content of the additive may be, for example, 0.01 to 10% by weight, preferably 0.1 to 5% by weight, based on the solid content of the shell composition of the capsule.

The capsule of the present invention has a shell thickness of 10 to 600 μm, preferably 30 to 400 μm, more preferably 40 to 250 μm after drying. Shell thicknesses of less than 10 μm lower shell strength and those of more than 600 μm decrease an amount of the content and do not give enough disintegration.

A size of the capsule of the present invention is not limited, but can generally be within the range of 0.3 to 10 mm in a diameter, preferably 1 to 8 mm. Capsule sizes of less than 0.3 mm are too small to cover sufficient amount of the content and those of more than 8 mm are difficult for a person to swallow down.

Producing Method of the Three-Layered Capsule

The three-layered capsule of the present invention is a seamless capsule having three-layered structure. The seamless capsule can be prepared by a dropping method using a multi-layer nozzle having not less than 3 layers, concretely a method using a triple nozzle and dropping into a cooling solution (such as JP S49-59789 A, JP S51-8176 A and JP S60-172343 A).

When a dropping method using the triple nozzle is used for producing the capsule of the present invention, the content is ejected from an innermost nozzle and the shell solution is ejected from the outermost nozzle, and the edible refined and processed oil is ejected from the intermediate nozzle as the protective layer. When ejecting, the solutions from the triple nozzle are simultaneously ejected at a certain rate into the cooling solution flowing at a certain speed to form a composite jet, thus releasing the jet into the cooling solution to continuously produce three-layered seamless capsules by surface tensions functioned between the shell solution and the cooling solution. When the triple nozzle is employed, the resulting capsule has three-layered structure of which the innermost layer contains the content. According to the present invention, since the non-hydrogenated oil is employed as the edible refined and processed oil when producing, cracks would be effectively prevented.

FIG. 1 shows a schematic view of a nozzle portion of an apparatus suitable for producing the three-layered seamless capsules, using a dropping method employing the triple nozzle.

FIG. 1 shows that a seamless capsule jet B is ejected from a nozzle section A and cut in a cooling solution 8 to form each seamless capsule 7. The nozzle section A concentrically includes an innermost nozzle 1, an intermediate nozzle 2 and an outermost nozzle 3, and a capsule content solution 4 is ejected from the innermost nozzle 1, a protective layer solution is ejected from the intermediate nozzle 2 (concretely between the intermediate nozzle 2 and the innermost nozzle 1) and a shell solution is ejected from the outermost nozzle 3 (concretely between the outermost nozzle 3 and the intermediate nozzle 2), thus the three solutions simultaneously ejecting to form the seamless capsule jet B.

The resulting seamless capsules are dried by air at a temperature of 5 to 30° C. for 2 to 12 hours. The capsules may be subjected to vacuum drying or vacuum-freeze drying after air drying, in order to have necessity of lowering a water content of the seamless capsules. The vacuum drying can be conducted at a vacuum degree under 0.002 to 0.5 MPa and the vacuum-freeze drying can be conducted at a temperature of not more than −20° C. Time period for the vacuum (freeze) drying is not limited, but can generally be conducted for 5 to 60 hours, preferably 24 to 48 hours. Periods of less than 5 hours dry the capsules insufficiently and water present in the shell adversely affects the content of the capsule.

The three-layered capsules obtained by the above method effectively prevent cracks when producing and reduce possibility of defective products in the producing step, thus leading to significant benefit, such as resource saving and waste eliminating. In addition, when the capsules are stored in a refrigerator to avoid high temperature in summer or when the capsules are added in yogurt, they have to keep in a circumstance of 0 to 10° C. and would easily generate cracking in a protective layer using conventional hardened oil and reduce protective effects of the content of the capsules, thus becoming poor storage stability. The three-layered capsules of the present invention, however, hardly generate cracking when they are stored in a low temperature condition. In the present application, the term "low temperature storage" means a storage in a temperature range of −80° C. to 10° C., preferably −40° C. to 8° C., more preferably −20° C. to 5° C.

The influence of cracks in the protective layer to capsule storage stability is that the cracks become passages between the content layer and the shell layer and the content layer leaks out to the shell layer over times and reaches to the outside of the capsules. On the contrary, water (including vapor), oxygen (including other gases) or the like invades into the capsule content from an outside atmosphere of the capsules, to reduce quantitative amount of the content of the capsule and deteriorate the content which is weak to water and oxygen, thus providing with problems of quality of the capsule.

The capsule using non-hydrogenated oil as the protective layer according to the present invention effectively inhibits cracks occurring in the protective layer and significantly increases storage stability. Accordingly, when the capsules are added in yogurt, the capsules are expected to prolong its expiration date. Further, to the customer who reacts with rejection against the "hydrogenated", capsule products which do not use the "hydrogenated" raw material can be provided and give big impact to them together with enhancement of stability, thus expanding consumption.

EXAMPLES

The present invention will be explained in detail by reference to examples. The present invention is not construed as limiting to the examples.

Example 1

(a) Content liquid: 19.0 parts by mass of *Bifidobacterium* powder were dispersed in 81.0 parts by mass of melted palm stearin (non-hydrogenated oil) having a melting point of 51° C. to form a content liquid.
(b) Protective layer liquid: 93.0 parts by mass of palm stearin (non-hydrogenated oil, melting point 53° C.) and 7.0 parts by mass of lecithin were mixed to form a protective layer liquid.
(c) Shell solution: 18.0 parts by mass of gelatin (jelly strength: 280 Bloom), 6.0 parts by mass of food additive glycerol, 1.0 part by mass of low methoxy (LM) pectin and 75.0 parts by mass of purified water were mixed to form a shell solution.

Using a concentric triple nozzle, the content liquid was ejected from the innermost nozzle, the protective layer liquid was ejected from the intermediate nozzle and the shell solution was ejected from the outermost nozzle, simultaneously into flowing cooling oil with dropwise to obtain three-layered seamless capsules P having a diameter of 6.5 mm. The resulting three-layered seamless capsules were air-dried at 20° C. for 8 hours. A mass ratio of content: protective layer:shell was 50%: 30%: 20%.

Example 2

Three-layered seamless capsules Q having a diameter of 6.5 mm containing *Bifidobacterium* were prepared as generally described in Example 1, with an exception that the protective layer liquid was changed to a mixture of 93.0 parts by mass of palm olein (non-hydrogenated oil and melting point of 24° C.) and 7.0 parts by mass of lecithin. The resulting three-layered seamless capsules were air-dried at 20° C. for 8 hours. A mass ratio of content:protective layer:shell was 50%: 30% 20%.

Example 3

Three-layered seamless capsules R having a diameter of 6.5 mm containing *Bifidobacterium* were prepared as generally described in Example 1, with an exception that the content liquid (a) and the protective layer liquid (b) were changed as follow:
(a) Content liquid: 19.0 parts by mass of *Bifidobacterium* powder were dispersed in a melted solution of 65.0 parts by mass of palm stearin (non-hydrogenated oil) having a melting point of 51° C. and 16.0 parts by mass of palm olein (non-hydrogenated oil) to form a content liquid.
(b) Protective layer liquid: 75.0 parts by mass of palm stearin (non-hydrogenated oil, melting point 53° C.), 18.0 parts by mass of palm olein (non-hydrogenated oil, melting point 24° C.) and 7.0 parts by mass of lecithin were mixed to form a protective layer liquid.

The resulting three-layered seamless capsules were air-dried at 20° C. for 8 hours. A mass ratio of content:protective layer:shell was 50%: 30%: 20%.

Example 4

Three-layered seamless capsules S having a diameter of 6.5 mm containing *Bifidobacterium* were prepared as generally described in Example 1, with an exception that the content liquid (a) and the protective layer liquid (b) were changed as follow:
(a) Content liquid: 19.0 parts by mass of *Bifidobacterium* powder were dispersed in a melted solution of 73.0 parts by mass of palm stearin (non-hydrogenated oil) having a melting point of 51° C. and 8.0 parts by mass of palm super olein (non-hydrogenated oil) having liquid form at normal temperature to form a content liquid.
(b) Protective layer liquid: 84.0 parts by mass of palm stearin (non-hydrogenated oil, melting point 53° C.), 9.0 parts by mass of palm double olein (non-hydrogenated oil) having liquid form at normal temperature and 7.0 parts by mass of lecithin were mixed to form a protective layer liquid.

The resulting three-layered seamless capsules were air-dried at 20° C. for 8 hours. A mass ratio of content:protective layer:shell was 50%: 30%: 20%.

Example 5

Three-layered seamless capsules T having a diameter of 6.5 mm containing *Bifidobacterium* were prepared as generally described in Example 1, with an exception that the content liquid (a) and the protective layer liquid (b) were changed as follow:
(a) Content liquid: 19.0 parts by mass of *Bifidobacterium* powder were dispersed in a melted solution of 65.0 parts by mass of palm stearin (non-hydrogenated oil) having a melting point of 51° C. and 16.0 parts by mass of palm mid fraction (non-hydrogenated oil) having a melting point of 26° C. to form a content liquid.
(b) Protective layer liquid: 75.0 parts by mass of palm stearin (non-hydrogenated oil, melting point 53° C.), 18.0 parts by mass of palm mid fraction (non-hydrogenated oil) having a melting point of 26° C. and 7.0 parts by mass of lecithin were mixed to form a protective layer liquid.

The resulting three-layered seamless capsules were air-dried at 20° C. for 8 hours. A mass ratio of content:protective layer:shell was 50%:30%: 20%.

Example 6

Three-layered seamless capsules U having a diameter of 6.5 mm containing *Bifidobacterium* were prepared as generally described in Example 1, with an exception that the content liquid (a) and the protective layer liquid (b) were changed as follow:
(a) Content liquid: 19.0 parts by mass of *Bifidobacterium* powder were dispersed in a melted solution of 81.0 parts by mass of an ester-exchanged oil of palm fractioned oil (non-hydrogenated oil) having a melting point of 38° C. to form a content liquid.
(b) Protective layer liquid: 93.0 parts by mass of an ester-exchanged oil of palm fractioned oil (non-hydrogenated oil, melting point 43° C.) and 7.0 parts by mass of lecithin were mixed to form a protective layer liquid.

The resulting three-layered seamless capsules were air-dried at 20° C. for 8 hours. A mass ratio of content:protective layer:shell was 50%: 30%: 20%.

SFC (%) of the non-hydrogenated oils employed in Examples 1 to 6 are listed in Table 1.

TABLE 1

|  | 10° C. | 20° C. | 30° C. | 40° C. | 45° C. |
| --- | --- | --- | --- | --- | --- |
| Palm Stearin | 67 | 55 | 37 | 25 | 23 |
| Palm Olein | 33 | 9 | 0.1 |  |  |
| Palm Mid-fraction | 59 | 40 | 2 | 0.3 |  |
| Ester-exchanged Palm Oil | 77 | 67 | 50 | 27 | 19 |
| Ester-exchanged Palm Olein | 35 | 25 | 14 | 7 | 0.3 |

The palm super olein and palm double olein are liquid oil at normal temperature, respectively.

Comparative Example 1

(a) Content liquid: 19.0 parts by mass of *Bifidobacterium* powder were dispersed in a melted solution of 81.0 parts by mass of hardened oil (hydrogenated oil) having a melting point of 39° C. to form a content liquid.
(b) Protective layer liquid: 93.0 parts by mass of hardened oil (hydrogenated oil, melting point 44° C.) and 7.0 parts by mass of lecithin were mixed to form a protective layer liquid.
(c) Shell solution: 18.0 parts by mass of gelatin (jelly strength: 280 Bloom), 6.0 parts by mass of food additive glycerol, 1.0 part by mass of low methoxy (LM) pectin and 75.0 parts by mass of purified water were mixed to form a shell solution.

Using a concentric triple nozzle, the content liquid was ejected from the innermost nozzle, the protective layer liquid was ejected from the intermediate nozzle and the shell solution was ejected from the outermost nozzle, simultaneously into flowing cooling oil with dropwise to obtain three layered seamless capsules W having a diameter of 6.5 mm. The resulting three-layered seamless capsules were air-dried at 20° C. for 8 hours. A mass ratio of content:protective layer:shell was 50%: 30%: 20%.

Figures 1, 3:
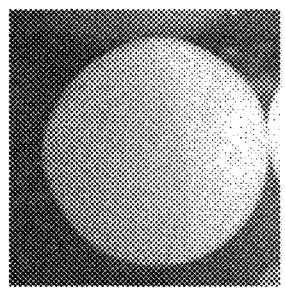
Figures 2, 3:
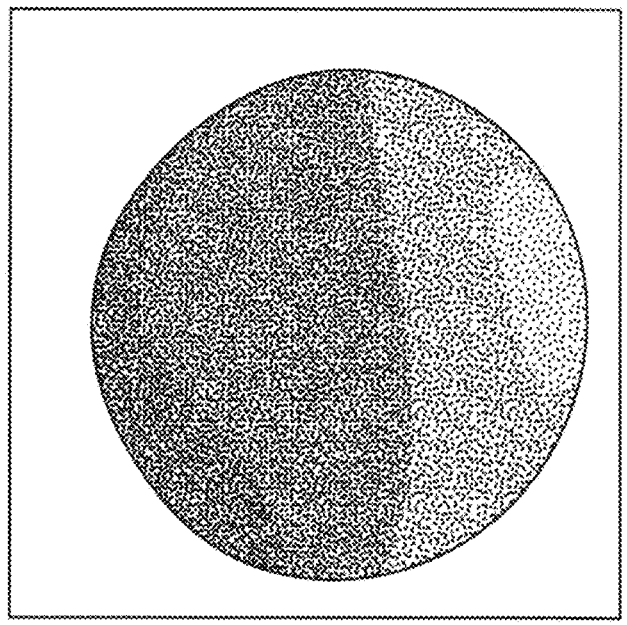
Figures 1, 4:
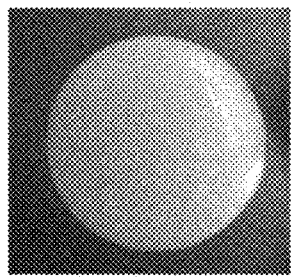
Figures 2, 4:
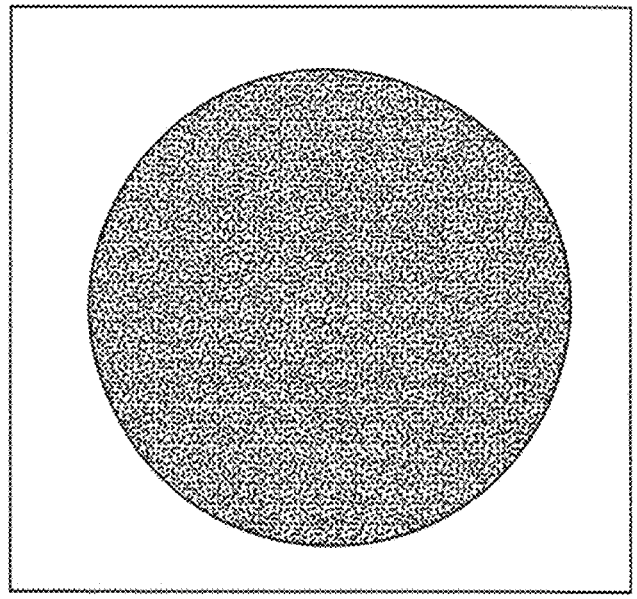

Each 100 particles of the three-layered capsules P to U containing *Bifidobacterium* of Examples and the three-layered capsules W containing *Bifidobacterium* were stored at 10° C. for 24 hours and cracking of the particles was examined, to find cracking in 8 to 10 particles of the seamless capsules W of Comparative Example 1. (see FIGS. 2 and 3). There was no cracking in each 100 particles of the three-layered seamless capsules P to U of Examples (see FIG. 4). FIGS. 2-1 and 3-1 show an enlarged photograph of the three-layered seamless capsule W of Comparative Example 1, which were taken in different angle to easily view the cracking, and FIGS. 2-2 and 3-2 are their schematic drawings as they are difficult to view the cracking. FIG. 4-1 shows an enlarged photograph of the three-layered seamless capsule P of Example 1 which does not have cracking, and FIG. 4-2 is its schematic drawing similar to FIGS. 2-2 and 3-2.

As is apparent from a comparison of Examples 1 to 6 with Comparative Example 1, when the non-hydrogenated oil of the present invention is employed, the cracking of the resulting three-layered seamless capsules does not occur for 100 particles and it shows excellent cracking inhibition. On the other hand, Comparative Example 1 which employs conventional hydrogenated oil for the protective layer shows cracking on 8 to 10 particles in 100 particles and arises production losses. It should be noted that the cracking of the protective layer in Comparative Example 1 can be clearly viewed at not more than 10° C. as the photograph, but it is difficult to view or to find the cracking when they are in circumstances of more than 10° C. However, when they are cooled to the conditions of not more than 10° C., the cracking easily reproduces. These phenomena can be considered to look like curing the cracking by entering at an elevated temperature the low melting point oil into the cracking generated in the solid oil at low temperature.

INDUSTRIAL APPLICABILITY

In the present invention, by employing edible refined and processed oil, especially non-hydrogenated oil as the protective layer of the three-layered capsules, defective products which have cracking which is generated in production or when storing at a low temperature are significantly prevented. The present invention reduces defective product loss and achieves save resources and enhance of storage stability. In addition, when the capsule products are stored at a refrigerator or the capsules are added in yogurt, they are generally stored at a temperature of 0 to 10° C. and would generate cracking in its protective layer to reduce protective effects of the content of the capsules and to deteriorate storage stability. In the present invention, non-hydrogenated oil is employed in the protective layer and effectively prevents cracking of the protective layer to lead to enhance storage stability of the capsules. When the capsule is added in yogurt, stability over time of the capsule content is enhanced to prolong its expiration date of the yogurt capsule products. Further, the non-hydrogenated oil is not a hydrogenated oil and, when it is employed in food products, consumers who do not like what "hydrogenated oil" was used as components are acceptable without problems.

REFERENCE SIGNS LIST

A Nozzle section
B Seamless capsule jet
1 Innermost nozzle
2 Intermediate nozzle
3 Outermost nozzle
4 Capsule content liquid
5 Protective layer liquid
6 Shell solution
7 Three-layered seamless capsule
8 Cooling solution

The invention claimed is:
1. A three-layered capsule which comprises:
 a content comprising an agent dispersed or solubilized in oil material, the agent having physiological activity,
 a protective layer, formed on the content, comprising a first edible refined and processed oil, and
 a shell, formed on an outside of the protective layer, comprising natural polymer, the three layers being present concentrically, wherein
 the oil material is selected from the group consisting of edible plant oil, a second edible refined and processed oil, sucrose fatty acid ester, glycerol fatty acid ester and a mixture thereof,
 the first edible refined and processed oil is a non-hydrogenated oil having a melting point of 15 to 55° C. and a solid fat content (SFC) of 30 to 90% at 10° C., 0.3 to 80% at 20° C., 0.1 to 70% at 30° C., 0.3 to 40% at 40° C., 0.3 to 30% at 45° C.,
 the first edible refined and processed oil is contained in an amount of not less than 75 parts by mass and not more than 93 parts by mass based on 100 parts by mass of the protective layer,
 the non-hydrogenated oil is palm stearin, which is fractionated from palm oil, and
 the protective layer has a melting point that is 2 to 9° C. higher than that of the content.
2. The three-layered capsule according to claim 1, wherein the natural polymer is water soluble.
3. The three-layered capsule according to claim 1, wherein the natural polymer is selected from the group consisting of gelatin, agar, gellan gum, carrageenan, furcellaran, pectin, chitosan, alginic acid or salt thereof, curdlan, starch, modified starch, pullulan, mannan and a mixture thereof.
4. The three-layered capsule according claim 1, wherein the three-layered capsule is a seamless capsule.
5. The three-layered capsule according to claim 1, wherein the main agent is selected from the group consisting of *Bifidobacterium, Lactobacillus*, lactoferrin, nattokinase, vitamin C, vitamin B1, vitamin B2, vitamin B12 and a mixture thereof.
6. A process for producing the three-layered capsule according to claim 1, comprising ejecting into cooling solution formed from cooled liquid oil, a solution of a content from an innermost nozzle of a concentric triple nozzles, the content comprising an agent dispersed or solubilized in oil material, the agent having physiological activity, ejecting a protective layer solution comprising a first edible refined and processed oil from an intermediate layer outside of the innermost nozzle, and ejecting a solution of natural polymer comprising natural polymer from an outermost nozzle, in a droplet form, to form a three-layered capsule, wherein
 the oil material is selected from the group consisting of edible plant oil, a second edible refined and processed oil, sucrose fatty acid ester, glycerol fatty acid ester and a mixture thereof,
 the first edible refined and processed oil is non-hydrogenated oil having a melting point of 15 to 55° C. and a solid fat content (SFC) of 30 to 90% at 10° C., 0.3 to 80% at 20° C., 0.1 to 70% at 30° C., 0.3 to 40% at 40° C., 0.3 to 30% at 45° C.,
 the first edible refined and processed oil is contained in an amount of not less than 75 parts by mass and not more than 93 parts by mass based on 100 parts by mass of the protective layer,
 the non-hydrogenated oil is palm stearin, which is fractionated from palm oil, and
 the protective layer has a melting point that is 2 to 9° C. higher than that of the content.

7. The process of the three-layered capsule according to claim 6, wherein the natural polymer is water soluble.

8. The process of the three-layered capsule according to claim 6, wherein the natural polymer is selected from the group consisting of gelatin, agar, gellan gum, carrageenan, furcellaran, pectin, chitosan, alginic acid or salt thereof, curdlan, starch, modified starch, pullulan, mannan and a mixture thereof.

9. The process of the three-layered capsule according to claim 6, wherein the three-layered capsule is a seamless capsule.

10. The process of the three-layered capsule according to claim 6, wherein the main agent is selected from the group consisting of *Bifidobacterium, Lactobacillus*, lactoferrin, nattokinase, vitamin C, vitamin B1, vitamin B2, vitamin B12 and a mixture thereof.

11. The three-layered capsule according to claim 1, wherein the three-layered capsule does not crack when stored at temperature less than 10° C.

* * * * *